(12) United States Patent
Asada et al.

(10) Patent No.: US 6,500,990 B2
(45) Date of Patent: Dec. 31, 2002

(54) METHOD FOR PRODUCING JASMONATE DERIVATIVES AND INTERMEDIATES THEREOF

(75) Inventors: Takahiro Asada, Wakayama (JP); Yoshiharu Ataka, Wakayama (JP); Junji Koshino, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/804,227

(22) Filed: Mar. 13, 2001

(65) Prior Publication Data

US 2001/0049455 A1 Dec. 6, 2001

(30) Foreign Application Priority Data

Mar. 15, 2000 (JP) ........................................ 2000-071689
Mar. 15, 2000 (JP) ........................................ 2000-071690

(51) Int. Cl.⁷ .......................... C07C 45/00; C07C 69/74
(52) U.S. Cl. ........................ 568/341; 568/343; 568/347; 568/348; 568/355; 568/356; 560/122
(58) Field of Search ................................ 568/341, 343, 568/347, 348, 355, 356; 560/122

(56) References Cited

U.S. PATENT DOCUMENTS 4,260,830 A    4/1981   Wilson et al.

FOREIGN PATENT DOCUMENTS

| DE | 150 051 | 8/1981 |
|----|---------|--------|
| JP | 51-023240 | 2/1976 |
| JP | 56-147740 | 11/1981 |
| JP | 59-080625 | 5/1984 |
| JP | 5-092934 | 4/1993 |
| JP | 6-080606 | 3/1994 |

*Primary Examiner*—James O. Wilson
*Assistant Examiner*—Sikarl A. Witherspoon
(74) *Attorney, Agent, or Firm*—Oblon, Spivak, McClelland, Maier & Neustadt, P.C.

(57) ABSTRACT

A process for efficiently producing a 2-alkyl-2-cyclopentenone comprising reacting an amine and a hydrogen halide, which are present in a ratio ranging from 1.1:1 to 5:1, with a 2-alkylidene cyclopentanone to carry out an isomerization reaction. A process for producing a jasmonate derivative comprising reacting a 2-alkyl-2-cyclopentenone with a malonic acid diester.

6 Claims, No Drawings

METHOD FOR PRODUCING JASMONATE DERIVATIVES AND INTERMEDIATES THEREOF

TECHNICAL FIELD OF THE INVENTION

The present invention relates to a method for producing a 2-alkyl-2-cyclopentenone useful as a synthetic intermediate of a biologically active substance or a perfume as well as a method for producing a jasmonate derivative useful as a perfume material or a biologically active substance by using the same.

PRIOR ART

As a method for producing a 2-alkyl-2-cyclopentenone, for instance, there is a method which comprises obtaining a 2-alkylidene cyclopentanone by dehydrating reaction of a 2-(1-hydroxyalkyl)-cyclopentanone and then isomerizing this 2-alkylidene cyclopentanone. Among such a method, there is known a method for producing a 2-alkyl-2-cyclopentenone by bringing a hydrogen halide into contact with a 2-alkylidene cyclopentanone and there are also investigated variable improvements thereof (JP-A 59-80625 etc.).

In this method, however, it is impossible to obtain the product in a high yield without low concentration condition so that further improvements have been desired for industrial production. As this improved method therefor, there is also known a method using a hydrogen halide salt of an amine in place of the above-mentioned hydrogen halide (JP-A 6-80606). Even in this method, however, no sufficiently satisfactory yield can be obtained without adding a solvent in excess.

Further, those methods wherein a 2-(1-hydroxyalkyl)-cyclopentanone is dehydrated and isomerized at one stage are also known (JP-A 56-147740 and JP-A.5-92934). However, these methods have drawbacks such as longer reaction time, poor yield, much solvent and poor productivity.

JP-A 51-23240 discloses a method for producing a 2-alkyl-2-cyclopentenone with a hydrogen halide or sulfonic acid.

DISCLOSURE OF THE INVENTION

The object of the present invention is to provide a method for efficiently producing a 2-alkyl-2-cyclopentenone as well as a method for producing a jasmonate derivative by using the same.

The present invention relates to a method for producing a 2-alkyl-2-cyclopentenone represented by the formula (2) (referred to hereinafter as the compound (2)):

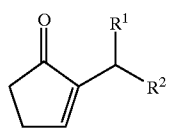

(2)

wherein each of $R^1$ and $R^2$ represents a hydrogen atom or a linear or branched alkyl group having 1 to 8 carbon atoms, or $R^1$ and $R^2$ may be formed into a cyclopentane or cyclohexane ring together with a bonded carbon atom, which comprises reacting an amine and a hydrogen halide with a 2-alkylidene cyclopentanone represented by the formula (1) (referred to hereinafter as the compound (1)) at a molar ratio of the amine/the hydrogen halide of from 1.1/1 to 5/1 to carry out isomerization reaction:

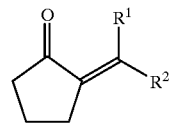

(1)

wherein $R^1$ and $R^2$ have the same meanings as defined above, as well as it relates to a method for producing the compound (2), which comprises reacting a catalyst comprising an amine and a hydrogen halide with a 2-(1-hydroxyalkyl)-cyclopentanone represented by the formula (3) (referred to hereinafter as the compound (3)) to carry out dehydration-isomerization reaction:

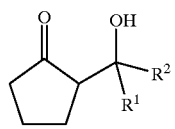

(3)

wherein $R^1$ and $R^2$ have the same meanings as defined above.

Further, the present invention relates to a method for producing a jasmonate derivative represented by the formula (5) (referred to hereinafter as the compound (5)):

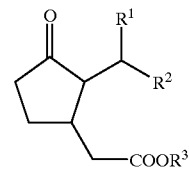

(5)

wherein $R^1$ and $R^2$ have the same meanings as defined above, $R^3$ represents a linear or branched alkyl group having 1 to 3 carbon atoms, which comprises reacting the compound (2) obtained in the method described above with a malonic acid diester represented by the formula (4) (referred to hereinafter as the compound (4)):

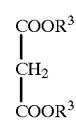

(4)

wherein $R^1$, $R^2$ and $R^3$ have the same meanings as defined above, and the two $R^3$ groups may be the same or different, and then reacting water therewith.

Furthermore, the present invention also provides use of the 2-alkyl-2-cyclopentenone obtained by the method described above as an intermediate for a jasmonate derivative.

MODE FOR CARRYING OUT THE INVENTION

[Method 1: The Method for Producing the Compound (2) Obtained from the Compound (1)]

The compound (1) used in the present invention can be produced by a publicly known method in the conventional art. For example, it can be easily synthesized by a method for condensing an enamine of cyclopentanone with an aldehyde and then decomposing the dehydrated-condensed product with an acid; a method of dehydrating the compound (3); or the like.

The compound (1) includes 2-butylidene cyclopentanone, 2-(2'-methylbutylidene) cyclopentanone, 2-pentylidene cyclopentanone, 2-hexylidene cyclopentanone, 2-cyclopentylidene cyclopentanone, 2-cyclohexylidene cyclopentanone and 2-(1'-methylbutylidene)-cyclopentanone.

The amine and hydrogen halide used in the present method at are reacted at a molar ratio of the amine/the hydrogen halide of from 1.1/1 to 5/1, preferably 1.2/1 to 3/1 and more preferably 1.5/1 to 3/1 in order to obtain the compound (2) in a high yield even in a small amount of a solvent.

The amine used in the present method is preferably a weakly basic aromatic amine or heterocyclic aromatic amine. Specifically, there may be exemplified aniline, diphenylamine, pyridine, picoline, quinoline and polyvinyl pyridine. Pyridine, picoline or quinoline is particularly preferable. The hydrogen halide may be hydrogen chloride, hydrogen bromide or hydrogen iodide. Hydrogen chloride or hydrogen bromide is particularly preferable.

The amine and hydrogen halide may be previously mixed at the ratio described above having the excess amine in order to use the mixture. On the other hand, the amine and hydrogen halide may be added to a reaction vessel at the ratio described above. The amount of the hydrogen halide used is preferably 1 to 50 mol-% and particularly preferably 2 to 20 mol-% as compared with the compound (1).

The reaction is preferably carried out in an alcohol solvent or under no solvents. As the alcohol solvent, e.g. $C_{1-8}$ lower alcohols, diols or triols are used. $C_{1-8}$ lower alcohols are particularly preferable. Specially, examples thereof include methanol, ethanol, 1-propanol, 2-propanol, butanol, pentanol, hexanol, 2-ethylhexanol, cyclohexanol, ethyleneglycol, 1,8-octanediol, glycerol and polyethyleneglycol. The amount of the solvent used is preferably 0.5 to 5 times and economically more preferably 0.5 to 2 times the weight of the compound (1). The reaction solvent is suitably selected depending on the physical properties of the compound (1) to be used. If the boiling point of the selected solvent is the reaction temperature or less, the reaction may be carried out under pressurization.

The reaction temperature is preferably 80 to 200° C. and particularly preferably 100 to 180° C., and the reaction is carried out for a suitable time and, after the reaction is finished, a work-up is carried out according to a usual manner, whereby the compound (2) can be obtained.

The compound (1), the solvent, the amine and the hydrogen halide can be simultaneously introduced and reacted, but the reaction procedure is preferably that, when the reaction temperature is reached, the compound (1) is brought into contact with the catalyst. This procedure includes a method which comprises introducing the compound (1) and the solvent, then adding dropwise a mixed solution of the amine and the hydrogen halide thereto at a predetermined temperature and reacting them and a method which comprises previously introducing the solvent, the amine and the hydrogen halide and then adding dropwise the compound (1) thereto at a predetermined temperature. Any method thereof may be adopted.

[Method 2: The Method for Producing the Compound (2) Obtained from the Compound (3)]

In the compound (3) used as the starting material in the present method, the alkyl group constituting 1-hydroxyalkyl group includes e.g. methyl group, ethyl group, propyl group, isopropyl group, butyl group, isobutyl group, amyl group, isoamyl group, hexyl group and heptyl group.

This compound (3) can be produced by a publicly known method in the conventional art. For example, it can be obtained by reacting cyclopentanone with an aldehyde or ketone represented by the formula (6):

(6)

wherein $R^1$ and $R^2$ have the same meanings as defined above.

The catalyst used in the present method comprises an amine and hydrogen halide. The amine may be more than enough to form a salt with the hydrogen halide and is not particularly limited but is preferably a weakly basic aromatic amine or heterocyclic aromatic amine. Specifically, it includes those described in the item of Method 1 and is particularly preferably pyridine, picoline or quinoline. The hydrogen halide includes those described in the item of Method 1 and is particularly preferably hydrogen chloride or hydrogen bromide.

The amine and hydrogen halide may be previously formed into a salt to be used. On the other hand, the amine and hydrogen halide may be added to a reaction vessel. The ratio of the amine to the hydrogen halide in the reaction system is preferably that the amine is used in excess. The molar ratio of the amine/the hydrogen halide is preferably from 1/1 to 5/1, more preferably from 1.1/1 to 5/1 and most preferably 1.2/1 to 3/1.

The catalyst comprising the amine and hydrogen halide is preferably added at such a ratio that the amount of the hydrogen halide is 5 to 50 mol-% as compared with the compound (3).

The reaction in the present method in no solvents, but a solvent is preferably used to prevent polymerization as side reaction. The solvent is preferably a polar solvent such as alcohols, diols and triols. Specially, examples of the solvent include those described in the item of Method 1. A $C_{4-8}$ alcohol is particularly preferable.

The amount of the solvent used is preferably 0.5 to 5 times and economically more preferably 0.5 to 2 times the weight of the compound (3). The solvent is suitably selected in consideration of the physical properties of the compound (3) and the reaction temperature.

With regard to the reaction temperature, from the viewpoint of finishing the reaction in a short time and improving the yield by preventing polymerization of compound (1) and/or (2), the reaction temperature is preferably 100 to 200° C. and particularly preferably 130 to 160° C. The reaction proceeds at an ordinary pressure but, if the reaction temperature is low, the reaction is preferably carried out under a reduced pressure so that water generated therein can be efficiently distilled away to the outside of the system.

The reaction in the present method is preferably carried out while water generated therein is distilled away. It is preferable in the reaction procedure that, when the reaction temperature is reached, the compound (3) is brought into contact with the catalyst. Because this procedure includes a method for adding dropwise the compound (3) to a mixed solution of the catalyst and the solvent and a method for adding dropwise the catalyst to a mixed solution of the compound (3) and the solvent, any method thereof may be selected.

After the reaction in the present method is finished, a work-up is carried out according to a usual manner, whereby the compound (2) can be obtained.

[Method for Producing the Compound (5)]

By using the compound (2) obtained in Method 1 or 2 described above as the starting material, the compound (5) useful as a perfume material or a biologically active substance can be obtained in a method described in e.g. EP 33604.

Specifically, the compounds (2) and (4) are firstly reacted in the presence of a basic catalyst to obtain a compound represented by the formula (7) (referred to hereinafter as the compound (7)):

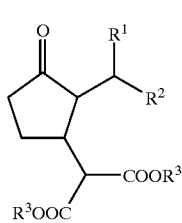

(7)

wherein $R^1$, $R^2$ and $R^3$ have the same meanings as defined above.

The compound (4) is preferably reacted at 1 to 5 times and preferably 1.2 to 2 times the mole of the compound (2).

The basic catalyst includes an alkali metal such as sodium and potassium and an alkali metal alkoxide such as a sodium alkoxide and a potassium alkoxide. The catalyst is preferably used in a 0.02- to 0.2-fold molar amount per the compound (2). The solvent is preferably a polar solvent such as alcohols. The reaction temperature is preferably in the range of −10° C. to 30° C. and more preferably in the range of 0 to 20° C.

Then, the obtained compound (7) is reacted with water, whereby the compound (5) can be produced. The reaction is preferably carried out while water is added dropwise to the reaction system in a 1- to 3-fold molar amount per the compound (7). The reaction temperature is preferably in the range of 150 to 220° C.

According to the method of the present invention, a 2-alkyl-2-cyclopentenone could be obtained in a high yield even if a solvent is not added in excess. Further, the 2-alkyl-2-cyclopentenone obtained in this method can be used as the starting material to produce a jasmonate derivative efficiently.

EXAMPLES

Example 1

19.0 g (0.125 mol) of 2-pentylidene cyclopentanone were dissolved in 19.0 g of n-butanol and heated to 130° C. Then, a mixed solution comprising 1.8 g (0.019 mol) of 3-picoline and 1.3 g (0.013 mol) of a 35% hydrochloric acid was added dropwise thereto for 30 minutes at the same temperature. After this dropping addition was finished, the resultant mixture was stirred for 3.5 hours under heating at the same temperature. After the reaction was finished, the mixture was cooled to the room temperature and neutralized with an aqueous solution of sodium hydroxide. Then, the resultant organic layer was analyzed by a gas chromatography [The analysis was carried out by using a DB-WAX column with tridecane added as the standard substance. Heating condition: from 60 to 220° C. by 5° C./min]. As the result, it was found that 15.8 g of 2-pentyl-2-cyclopentenone were contained in the product after the reaction was finished (yield: 83.2%).

Example 2

15.5 g of 2-pentyl-2-cyclopentenone were obtained (yield: 81.7%) in the same manner as in Example 1 except that a mixed solution comprising 2.3 g (0.025 mol) of 3-picoline and 1.3 g (0.013 mol) of a 35% hydrochloric acid was used.

Example 3

15.0 g of 2-pentyl-2-cyclopentenone were obtained (yield: 78.6%) in the same manner as in Example 1 except that a mixed solution of 4.7 g (0.050 mol) of 3-picoline and 1.3 g (0.013 mol) of a 35% hydrochloric acid was used.

Comparative Example 1

14.3 g of 2-pentyl-2-cyclopentenone were obtained (yield: 75.2%) in the same manner as in Example 1 except that a mixed solution comprising 1.2 g (0.013 mol) of 3-picoline and 1.3 g (0.013 mol) of a 35% hydrochloric acid was used.

Example 4

15.09 g (0.16 mol) of 3-picoline and 5.63 g (0.055 mol) of a 35% hydrochloric acid were mixed with 82.2 g of n-hexanol and heated to 160° C. Then, 164.4 g (1.08 mol) of 2-pentylidene cyclopentanone were added dropwise thereto at the same temperature for 2 hours and a 35% hydrochloric acid was simultaneously added dropwise thereto at the rate of 1.41 g (0.014 mol)/h for 2 hours. After the dropping addition was finished, the resultant mixture was stirred for 5 hours under heating at the same temperature while the 35% hydrochloric acid was continuously added dropwise. After the reaction was finished, the mixture was cooled to the room temperature and neutralized with an aqueous solution of sodium hydroxide. Then, the resultant organic layer was analyzed in the same manner as in Example 1. As the result, 148.3 g of 2-pentyl-2-cyclopentenone were obtained (yield: 90.2%).

Example 5

144.7 g of 2-pentyl-2-cyclopentenone were obtained (yield: 88.0%) in the same manner as in Example 4 except that 82.2 g of 2-ethylhexanol were used as the solvent.

Example 6

5.44 g (0.058 mol) of 3-picoline and 5.54 g (0.053 mol) of a 35% hydrochloric acid were mixed with 100.0 g of 2-ethylhexanol and heated to 140° C. Then, 100.0 g (0.53 mol) of 2-pentylidene cyclopentanone were added dropwise thereto for 2 hours at the same temperature. After this dropping addition was finished, the resultant mixture was stirred for 2 hours under heating at the same temperature. After the reaction was finished, the mixture was cooled to the room temperature and neutralized with an aqueous solution of sodium hydroxide. Then, the resultant organic layer was analyzed in the same manner as in Example 1. As the result, 69.2 g of 2-pentyl-2-cyclopentenone were obtained (yield: 86.0%).

Example 7

In accordance with Example 6, the reaction with dropping addition was carried out by using 7.42 g (0.080 mol) of 3-picoline and 5.54 g (0.053 mol) of a 35% hydrochloric acid. After the dropping addition was finished, the resultant mixture was stirred for 5 hours under heating at the same temperature. After the reaction was finished, the mixture was cooled to the room temperature and neutralized with an aqueous solution of sodium hydroxide. Then, the resultant organic layer was analyzed in the same manner as in Example 1. As the result, 65.2 g of 2-pentyl-2-cyclopentenone were obtained (yield: 80.8%).

Example 8

23.5 g of n-hexanol were placed into a reactor equipped with a Dean-Stark trap. 1.8 g (0.019 mol) of 3-picoline and 1.3 g (0.013 mol) of a 35% hydrochloric acid were mixed therewith and heated to 140° C. Then, 21.3 g (0.125 mol) of 2-(1-hydroxypentyl)-cyclopentanone were added dropwise thereto for 3 hours at the same temperature. During the reaction, the distillate was separated into 2 layers by the Dean-Stark trap, and the aqueous layer was removed to the outside of the system, while the organic layer was refluxed in the reaction system, in order to carry out the reaction. After the dropping addition was finished, the resultant mixture was stirred for 3 hours under heating at the same temperature. After the reaction was finished, the mixture was cooled to the room temperature and neutralized with an aqueous solution of sodium hydroxide. Then, the organic layer was analyzed by a gas chromatography [The analysis was carried out by using a DB-WAX column with tridecane added as the standard substance. Heating condition: from 60 to 220° C. by 5° C./min]. As the result, it was found that 15.8 g of 2-pentyl-2-cyclopentenone were contained in the product after the reaction was finished (yield: 83.2%).

Example 9

15.4 g of 2-pentyl-2-cyclopentenone were obtained (yield: 81.1%) in the same manner as in Example 8 except that 2.4 g (0.026 mol) of 3-picoline and 2.6 g (0.025 mol) of a 35% hydrochloric acid were mixed with 12.7 g of 2-ethylhexanol and reacted at 160° C.

Example 10

7.4 g (0.079 mol) of 3-picoline and 5.4 g (0.053 mol) of a 35% hydrochloric acid were mixed with 125.0 g of n-hexanol and heated to 160° C. Then, 180.5 g (1.06 mol) of 2-(1-hydroxypentyl)-cyclopentanone were added dropwise thereto at the same temperature for 2 hours and a 35% hydrochloric acid was simultaneously added dropwise thereto at the rate of 1.4 g (0.014 mol) /h. After the dropping addition was finished, the resultant mixture was stirred for 3 hours under heating at the same temperature while the 35% hydrochloric acid was continuously added dropwise. After the reaction was finished, the mixture was cooled to the room temperature and neutralized with an aqueous solution of sodium hydroxide. Then, the resultant organic layer was analyzed in the same manner as in Example 8. As the result, it was found that 144.7 g of 2-pentyl-2-cyclopentenone were contained in the product after the reaction was finished (yield: 89.7%).

Example 11

139.7 g of 2-pentyl-2-cyclopentenone were obtained (yield: 86.6%) in the same manner as in Example 10 except that 62.5 g of n-hexanol were used as the solvent.

Example 12

42.6 g of 2-(1-hydroxypentyl)-cyclopentanone were dissolved in 45.4 g of n-butanol and heated to 130° C. Then, a mixed solution comprising 4.7 g (0.050 mol) of 3-picoline and 4.9 g (0.048 mol) of a 35% hydrochloric acid was added dropwise thereto for 30 minutes at the same temperature. After this dropping addition was finished, the resultant mixture was stirred for 3.5 hours under heating at the same temperature. After the reaction was finished, the mixture was cooled to the room temperature and neutralized with an aqueous solution of sodium hydroxide. Then, the resultant organic layer was analyzed in the same manner as in Example 8. As the result, it was found that 28.8 g of 2-pentyl-2-cyclopentenone were contained in the product after the reaction was finished (yield: 75.6%).

Example 13

27.7 g of 2-pentyl-2-cyclopentenone were obtained (yield: 72.9%) in the same manner as in Example 12 except that the reaction was carried out by adding dropwise a mixed solution comprising 6.5 g (0.050 mol) of quinoline and 4.9 g (0.048 mol) of a 35% hydrochloric acid.

Example 14

32.8 g of 2-pentyl-2-cyclopentenone were obtained (yield: 86.2%) in the same manner as in Example 12 except that the reaction was carried out at 160° C. for 1.5 hour by adding dropwise a mixed solution comprising 4.0 g (0.051 mol) of pyridine and 4.9 g (0.048 mol) of a 35% hydrochloric acid with using 45.4 g of n-hexanol as the solvent.

Comparative Example 2

42.6 g of 2-(1-hydroxypentyl)-cyclopentanone were dissolved in 161.9 g of n-butanol and heated to 130° C. Then, 24.5 g (0.24 mol) of a 35% hydrochloric acid were added dropwise thereto for 30 minutes at the same temperature. After the dropping addition was finished, the resultant mixture was stirred for 2 hours under heating at the same temperature. After the reaction was finished, the mixture was cooled to the room temperature and neutralized with an aqueous solution of sodium hydroxide. Then, the resultant organic layer was analyzed in the same manner as in Example 8. As the result, 22.9 g of 2-pentyl-2-cyclopentenone were obtained (yield: 60.0%).

Example 15

236 g (1.8 mol) of dimethyl malonate were dissolved in 76 g of absolute methanol under an atmosphere of nitrogen and cooled to 0° C. 12.9 g (0.072 mol) of sodium methoxide (as a solution in a 30% methanol) were added thereto and then 190 g (1.2 mol) of 2-pentyl-2-cyclopentenone obtained by the synthesis in the same manner as in Example 1 were added dropwise thereto at 0° C. for 2 hours. After this dropping addition was finished, unreacted dimethyl malonate was distilled away under a reduced pressure to obtain 320 g of product.

The product obtained above was added to a reaction device equipped with a distillation tube and heated to 215° C. Water was added dropwise thereto at the rate of 6.4 g/h (2%/h). While the carbon dioxide and the methanol generated therein were distilled away, the reaction with the dropping addition was carried out at 215° C. for 4 hours. After the reaction was finished, 245 g of methyl 3-oxo-2-pentylcyclopentyl acetate were obtained in 251 g of the crude product (yield in the 2 steps: 76%).

Methyl 3-oxo-2-pentylcyclopentyl acetate obtained by fractionating (or rectifying) the crude product had a fruity and jasmine scent and was also excellent as a perfume material.

Example 16

Using 2-pentyl-2-cyclopentenone obtained by the synthesis in the same manner as in Example 8, methyl 3-oxo-2-pentylcyclopentyl acetate could be obtained in the exactly same way by synthesis in the same manner as in Example 15.

What is claimed is:

1. A method for producing a 2-alkyl-2-cyclopentenone represented by formula (2):

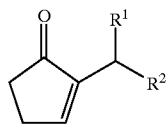

(2)

wherein each of $R^1$ and $R^2$ represents a hydrogen atom or a linear or branched alkyl group having 1 to 8 carbon atoms, or $R^1$ and $R^2$ may be formed into a cyclopentane or cyclohexane ring together with a bonded carbon atom, comprises reacting an amine and a hydrogen halide with a 2-alkylidene cyclopentanone represented by the formula (1) at a molar ratio of the amine/the hydrogen halide of from 1.1/1 to 5/1 to carry out an isomerization reaction:

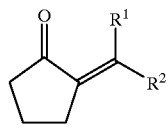

(1)

wherein $R^1$ and $R^2$ have the same meanings as defined above.

2. A method for producing the 2-alkyl-2-cyclopentenone represented by formula (2):

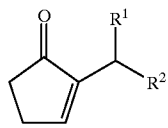

(2)

wherein $R^1$ and $R^2$ represents a hydrogen atom or a linear or branched alkyl group having 1 to 8 carbon atoms, or $R^1$ and $R^2$ may be formed into a cyclopentane or cyclohexane ring together with a bonded carbon atom, comprising reacting a catalyst comprising an amine and a hydrogen halide with a 2-(1-hydroxyalkyl)-cyclopentanone represented by formula (3) to carry out a dehydration-isomerization reaction:

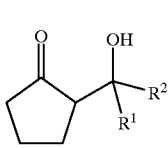

(3)

wherein $R^1$ and $R^2$ have the same meanings as defined above for formula (2).

3. The method of claim 1, wherein the amine is an aromatic amine or a heterocyclic aromatic amine.

4. A method for producing a 2-alkyl-2-cyclopentenone represented by formula (2):

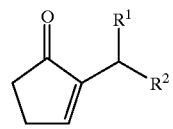

(2)

wherein each of $R^1$ and $R^2$ represents a hydrogen atom or a linear or branched alkyl group having 1 to 8 carbon atoms, or $R^1$ and $R^2$ may be formed into a cyclopentane or cyclohexane ring together with a bonded carbon atom, comprising reacting an amine and a hydrogen halide with a 2-alkylidene cyclopentanone represented by formula (1) at a molar ratio of the amine/the hydrogen halide of from 1.1/1 to 5/1 to carry out an isomerization reaction:

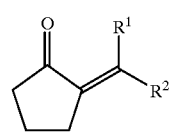

(1)

wherein $R^1$ and $R^2$ have the same meanings as defined above and, wherein the 2-alkylidene cyclopentanone represented by formula (1) is obtained by dehydration of the 2-(1-hydroxyalkyl)-cyclopentanone represented by formula (3).

5. A method for producing a jasmonate derivative represented by the formula (5):

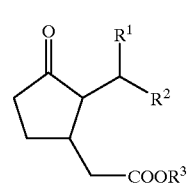

(5)

wherein $R^1$ and $R^2$ have the same meanings as defined in claim 1, $R^3$ represents a linear or branched alkyl group having 1 to 3 carbon atoms, comprising reacting the 2-alkyl-2-cyclopentenone represented by formula (2) obtained in the method described in claim 1 with a malonic acid diester represented by formula (4):

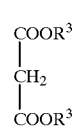

(4)

wherein $R^1$, $R^2$ and $R^3$ have the same meanings as defined above, and the two $R^3$ groups may be the same or different, and then reacting water therewith.

6. A method for producing a compound represented by formula (5):

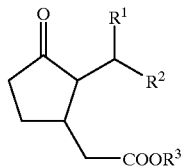

(5)

wherein $R^1$ and $R^2$ have the same meanings as defined in claim 2, $R^3$ represents a linear or branched alkyl group having 1 to 3 carbon atoms, comprising reacting the 2-alkyl-2-cyclopentenone represented by formula (2) obtained in the method described in claim 2 with a malonic acid diester represented by formula (4):

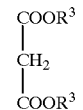

(4)

wherein $R^1$, $R^2$ and $R^3$ have the same meanings as defined above, and the two $R^3$ groups may be the same or different, and then reacting water therewith.

* * * * *